(12) United States Patent
Goulet et al.

(10) Patent No.: US 7,335,230 B2
(45) Date of Patent: Feb. 26, 2008

(54) CONNECTIVE TISSUE SUBSTITUTES, METHOD OF PREPARATION AND USES THEREOF

(75) Inventors: Francine Goulet, Sainte-Foy (CA); Denis Rancourt, Levis (CA); Rejean Cloutier, Sillery (CA); Julie Tremblay, Beauport (CA); Francois A. Auger, Sillery (CA); Albert Normand, deceased, late of Sainte-Foy (CA); Lucie German, St-Augustin (CA); Jean Lamontagne, St-Augustin (CA); Marc Bouchard, Sainte-Foy (CA); Eve Langelier, St-Etinne-de-Lauzon (CA); Daniel Dupuis, Sainte-Foy (CA); Stephane Bouchard, Hull (CA); Nazrul Islam, Sainte-Foy (CA); Louis-Mathieu Stevens, Montreal (CA); Sheila Laverty, St-Charles-sur-Richelieu (CA); Bertrand Lussier, St-Hyacinthe (CA); Anne-Marie Belzil, Outremount (CA); Pierrot Tremblay, Chicoutimi (CA)

(73) Assignee: Universite de Montreal, Montreal (CA)

( * ) Notice: Subject to any disclaimer, the term of this patent is extended or adjusted under 35 U.S.C. 154(b) by 0 days.

(21) Appl. No.: 09/990,320

(22) Filed: Nov. 23, 2001

(65) Prior Publication Data

US 2003/0100948 A1  May 29, 2003
US 2007/0005138 A9  Jan. 4, 2007

Related U.S. Application Data

(60) Provisional application No. 60/252,588, filed on Nov. 24, 2000.

(51) Int. Cl.
*A61F 2/08* (2006.01)

(52) U.S. Cl. .................................. 623/13.17
(58) Field of Classification Search ............... 623/11, 623/13
See application file for complete search history.

(56) References Cited

U.S. PATENT DOCUMENTS

| | | | | |
|---|---|---|---|---|
| 5,067,962 A | * | 11/1991 | Campbell et al. | 128/898 |
| 5,171,273 A | * | 12/1992 | Silver et al. | 623/13.11 |
| 5,356,435 A | | 10/1994 | Thein | |
| 5,445,833 A | * | 8/1995 | Badylak et al. | 424/551 |
| 5,613,982 A | * | 3/1997 | Goldstein | 424/423 |
| 5,718,012 A | | 2/1998 | Cavallaro | |
| 5,855,619 A | | 1/1999 | Caplan et al. | |
| 6,099,568 A | | 8/2000 | Simonian et al. | |
| 6,287,340 B1 | * | 9/2001 | Altman et al. | 623/13.11 |
| 6,293,970 B1 | | 9/2001 | Wolfinbarger et al. | |
| 6,416,995 B1 | | 7/2002 | Wolfinbarger | |
| 6,432,712 B1 | | 8/2002 | Wolfinbarger | |

(Continued)

FOREIGN PATENT DOCUMENTS

WO   WO9417851   8/1994

(Continued)

*Primary Examiner*—Corrine McDermott
*Assistant Examiner*—Christopher Daniel Prone

(57) ABSTRACT

The present invention relates to connective tissue substitute implant and method of preparation thereof. The implant is essentially composed of two bone anchors joined at the proximal ends by matrix layers and/or filaments coated by supplementary biocompatible matrix coating layer which can contain living stem cells isolated from injured connective tissue.

29 Claims, 17 Drawing Sheets

U.S. PATENT DOCUMENTS

| | | |
|---|---|---|
| 6,444,222 B1 | 9/2002 | Asculai et al. |
| 6,544,289 B2 | 4/2003 | Wolfinbarger et al. |
| 6,569,200 B2 | 5/2003 | Wolfinbarger et al. |
| 2002/0197718 A1 | 12/2002 | Myles et al. |
| 2003/0003153 A1 | 1/2003 | Asculai et al. |
| 2003/0083752 A1 | 5/2003 | Wolfinbarger et al. |
| 2003/0135284 A1 | 7/2003 | Crouch et al. |
| 2003/0217415 A1 | 11/2003 | Crouch et al. |
| 2003/0219417 A1 | 11/2003 | Wolfinbarger |

FOREIGN PATENT DOCUMENTS

| | | |
|---|---|---|
| WO | WO9745071 | 12/1997 |
| WO | WO 00/69355 | 11/2000 |
| WO | WO02089774 | 11/2002 |

* cited by examiner

CONNECTIVE TISSUE SUBSTITUTES, METHOD OF PREPARATION AND USES THEREOF

CROSS REFERENCE TO RELATED APPLICATION

This application claims the benefit, under 35 U.S.C. § 119(e), of U.S. provisional application No. 60/252,588 filed Nov. 24, 2000.

BACKGROUND OF THE INVENTION (a) Field of the Invention

The invention relates to the field of tissue engineering, production of connective tissue linked to natural bones or synthetic bone substitutes (tendons, ligaments, cartilage, etc.) can benefit from the invented procedure. The procedure of the present invention is carried out to produce bioengineered connective tissue substitutes. Connective tissue substitutes (CTS) of the invention may be constructed for replacement of ligaments, and most particularly cruciate ligaments or tendons.

(b) Description of Prior Art

Researchers in the surgical arts have been working for many years to develop new techniques and materials for use as grafts to replace or repair damaged or torn tissue structures, particularly bones and connective tissues, such as ligaments and tendons, and to hasten soft tissue repair. It is very common today, for instance, for an orthopedic surgeon to harvest a central portion of patellar tendon of autogenous or allogenous origin for use as a replacement for a torn cruciate ligament. The surgical methods for such approaches are well known. Further it has become common for surgeons to use implantable prostheses formed from plastic, metal and/or ceramic material for reconstruction or replacement of physiological structures. Yet despite their wide use, surgically implanted prostheses present many attendant risks to the patient. It will suffice to say that surgeons are in need of a non-immunogenic, high tensile strength graft material which can be used for surgical repair of bones, tendons, ligaments and other functional tissue structures.

One of the most widely used anterior cruciate ligament (ACL) substitutes is the bone-patellar tendon-bone graft. The central one-third of the patient's or a donor's patella tendon, along with portions of the bony insertions of the patella tendon, is used as a replacement for the damaged ACL. The bony insertions are harvested as bone fragments to facilitate implantation and fixation of the replacement graft into osseous tunnels performed in the tibia and femur in the patient's knee joint. The bone-patellar tendon-bone graft is a popular choice for ACL reconstructive surgery because of its high load strength after six weeks and its functional bone fixation.

Some fixation devices employ various structures for coupling with a ligament or a suture and for engaging with the bone. For example, U.S. Pat. No. 5,356,435 discloses an element for fixing a ligament in a bony tunnel. The element includes an internal conduit for receiving an end of a ligament, and a clamping structure for securing the ligament end within the conduit. U.S. Pat. No. 5,356,413 to Martins et al. discloses a surgical anchor having a body portion and a suture-receiving bone. Another commonly used ACL substitute is the iliotibial band graft. The iliotibial band is a section of ligament which is harvested from a portion of a patients or a donor's iliotibial ligament located within the anterolateral ligament structures of the knee joint. The major problem with these techniques is that another part of the body, or the joint of the donor is often significantly weakened after biopsied to get grafts. Long term drawbacks of this approach are that chronic pain, patellar fractures, knee instability and cartilage degeneration.

Researchers have been attempting to develop satisfactory polymers or plastic materials to serve as ligament or tendon for other connective tissues replacements. It has been found that it is difficult to provide long-term solution using these materials to permanently replace connective tissues.

Artificial materials based on network fibers made of polyester or polytetrafluoroethylene have been used extensively as replacements for ligament and tendon, with some success. However, persistent inflammatory reactions occur following wear off of particles upon time post-implantation. Additionally, they do not readily breakdown and are not readily integrated with the body via remodeling by tissue cells.

Bioengineered tissues can be used as grafts implants or prostheses to replace damaged tissues.

U.S. Pat. No. 5,855,619 of Caplan discloses the use of a filament as load-bearing member of a contracted gel matrix containing mesenchymal cells. The implant described in this patent allows partial repair of connective tissues by attaching the implant to the tissue to be repaired. However, since this implant is constructed without anchoring extremities, the anchorage capability is limited.

Fibroblast-populated Collagen gels (FPCG) constitute an interesting in vitro model of soft tissues to investigate tissue response to various biological, chemical, electrical, and mechanical stimuli. In the past year, the potential of using a ligament-shaped FPCG to produce a bioengineered anterior cruciate ligament (ACL) has been investigated. Mechanical properties of FPCG are known, however, to be significantly lower than those required for a functional ACL. Finding ways to improve their mechanical properties would be highly beneficial not only for improving a ACL but also for the tissue engineering field in general.

It is therefore an object of the present invention to provide an implant and method of preparation thereof which obviates the disadvantages of the prior art approaches.

SUMMARY OF THE INVENTION

One object of the present invention is to provide an implant for connective tissue substitution in a human or animal, comprising a pair of bone anchors joined at their proximal ends by at least one support filament, the filament being coated by at least one matrix layer of thickness sufficient to allow for colonization by cells.

Another object of the present invention is to provide method of preparing the implant for connective tissue substitution in an animal, which comprises the steps of providing a set of bone anchors by joining a pair of bone plugs at their proximal ends by at least one support filament; and incubating at least one time the set of bone anchors in a solution containing matrix forming molecules for a period time sufficient for the formation of at least one matrix layer around the filament, the matrix layer with thickness sufficient to allow for colonization by cells, wherein the incubation is performed under condition inducing waves, vibration, cyclic traction, and/or static traction of the implant.

According to another object of the present invention, there is provided a method of preparing an implant for connective tissue substitution in an animal, said method comprising the steps of:

a) providing a set of bone anchors by joining a pair of bone plugs at their proximal ends by at least one support filament; and b) incubating at least one time the set of bone anchors of step a) in a solution containing matrix forming molecules for a period time sufficient for the formation of at least one the matrix layer has a thickness sufficient to allow for colonization by cells, and wherein the incubation is performed under conditions in which are induced waves, vibrations, cyclic tractions, and/or static tractions of the implant.

In accordance with the present invention there is provided a matrix which is further colonized by cells. The cells may be autologous, heterologous, or cells selected from the group of fibroblast, myoblast, osteoblast, mesenchymal, endothelial, immune, chondrocyte cell, and combinations thereof.

Another object of the invention is to provide with connective tissue substitution that is partial or complete substitution of a connective tissue. The connective tissue may be selected from the group consisting of tendon, cartilage, disk, meniscus, muscle, tooth, hair, joint, ligament, and combinations thereof Furthermore, the filament and/or matrix layer may be dehydrated or lyophilized prior to implantation.

Also in accordance with the invention, the bone anchor may be selected from the group consisting of bone portion, and piece composed of natural and/or synthetic biocompatible porous material.

The matrix layer of the invention may be composed of products selected from the group consisting of chitosan, glycosaminoglycan, chitin, ubiquitin, elastin, polyethylen glycol, polyethylen oxide, vimentin, fibronectin, derivatives thereof, and combination thereof.

Also, the filament of the present invention may be selected from the group of resorbable thread, natural fibers, and filament composed of proteins, lipids, biocompatible molecules and/or synthetic components.

The implant of the invention may further comprises a pharmaceutically effective amount of biologically active molecule selected from the group of drugs, growth factors, cytokines, antibiotics, hormones, and combination thereof.

Another object of the invention is to provide a matrix layer further comprising at least one inner layer of gel and/or filament coated by at least one supplementary matrix coating layer, or an implant comprising an inner layer of matrix and/or filament which may be dehydrated or lyophilized prior coating with the supplementary matrix coating layer. In addition, the matrix-coating layer may further comprises cells.

For the purpose of the present invention the following terms are defined below.

The term "matrix" as used herein is intended to mean a network of biological extracellular constituents, as example but without limitation collagen, elastin, fibronectin, laminine, proteoglycans, glycosaminoglycans, chitosan, ubiquitin and derivatives thereof, in a hydrated or dehydrated form. This matrix can be produced with natural fibers in combination or not with synthetic or semi-synthetic fibers.

The term "graft", as used herein refers to a natural and/or synthetic implantable substitute for various tissue types.

The term "lyophylization" as used herein is intended to mean passive or active dehydration of hydrated matrix network as defined above. Simple air-drying, dessication, vacuum assisted dehydration, warming, water sublimation or other methods may perform the lyophilization.

The term "chemically fixed" as used herein is intended to mean fixation of treatment of matrix with a chemical, as for example but without limiting the invention, paraformaldehyde, ethanol, formaldehyde, methanol, to create link between the matrix fibers and the anchors, bones or bone substitutes.

This summary of the invention does not necessarily describe all necessary features of the invention, but that the invention may also reside in a sub-combination of these described features. The summary of the invention, thus incorporated, presents, therefore, only an example but not a limitation of subject matter to exactly this combination of features.

DETAILED DESCRIPTION OF THE INVENTION

Figure 1:
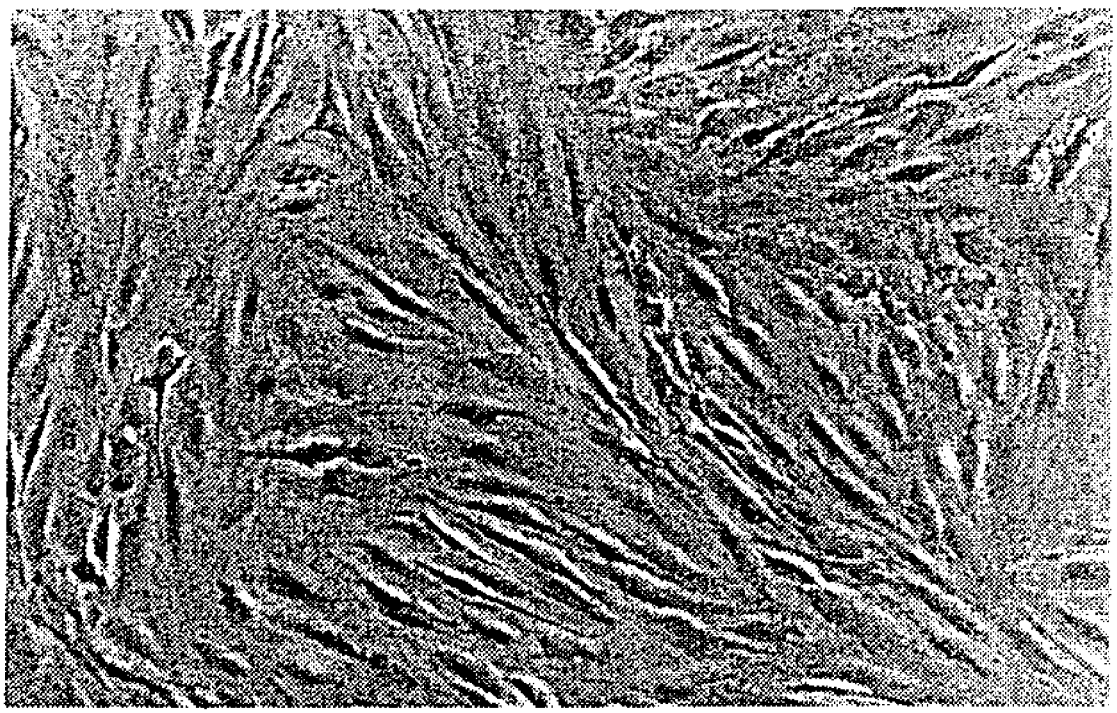
FIG. 1 illustrates ligament fibroblasts (LF) isolated from a human ACL biopsy.

The following description is of a preferred embodiment by way of example only and without limitation to the combination of features necessary for carrying the invention into effect.

In accordance with one embodiment of the invention, there is provided an implant allowing permanent implantation of a connective tissue substitute.

It is known in the art that synthetic prosthesis such as Dacron™ or Iad are susceptible indirectly to wear off particles in the knee joint within a few years, leading to inflammatory reactions, cartilage degeneration and functional instability of the knee.

In one embodiment, the implant of the invention doesn't present the risks of graft rejection as it is intended to use or integrate autologous cells from the host's connective tissues, their own bone fragments and collagen.

Another important embodiment of the invention is that the use of the instant implant avoids taking any portion of healthy autologous tissues, such as a part of the patellar, semitendinous or TFL iliotibial band, or semimembranous tendons for connective tissue replacement, which often lead to chronic pain, muscular weakness or instability of the joints. Only some cells are removed from its host, defatted if necessary and processed in one of several well-known procedures used to prepare the tissue for implantation into a human, an animal, as for example but without limitation, horses, dogs and other domestic animals. The invention applies also in a general manner in the fields of veterinarian, dentistry, and orthodontic cares.

The cells useful to contract the collagen fibrils during the formation of an organized tissue-substitute implant can be obtained from various mammalian sources (e.g., bovine, porcine, human, canine). The connective tissue cells used in the method of the present invention were fibroblasts, but other mesenchymal cell types, such as fibroblasts of other sources and tissues may also be used. The human fibroblasts can be isolated by enzymatic disaggregation, explants or perfusion of the tissues of origin.

Naturally occurring cells in accordance with the present invention may include, but not limited to epithelial cells, myoblasts, chondroblasts, osteoblasts, fibroblasts, and other fibrous connective cells coming from tendon, ligament, cartilage, and the like.

Also, the autologous connective tissue cells may be conserved in a cell depository to prepare another bioengineered connective tissue implant for the patients who would break the graft under subsequent traumatic circumstances.

In accordance with another embodiment of the present invention, the procedure of implantation may be performed by arthroscopy, avoiding arthrotomies and associated risks (infection, knee pain, and loss of articular mobility, major swelling and permanent scar). These advantages contribute to reduce the cost of medical care on a long-term basis and improve life quality of the patients post-surgery.

In another embodiment, a fully functional replacement tissue is able to withstand at least the stresses and strains imposed by normal bodily activity on the type of tissue the construct is to replace.

Furthermore, in accordance with one embodiment of the invention, the implant is fully biocompatible and integrable, in vivo, i.e., the implant resembles a natural tissue so as to be colonized by cells and interact with these specific cells already present in the body. The colonizing cells further organize the implant and secrete specific products, such as extracellular matrix constituents, proteins and/or growth factors, within the connective tissue substitute of the present invention, enabling it to degrade, remodel and regenerate the histological structures as a functional tissue substitute. Such integration may strengthen and conditions the implant to better performs as a substitute tissue.

Yet in accordance with another aspect of the present invention, the gel layer of the implant may be supplemented with proteins, peptides, or hormones playing roles during tissue integration and tissue repair. Several known factors may be released from the implant prior implantation, as, but not limited to growth factors, growth hormones, fibroblast growth factor, epithelial growth factor, TGF-beta, insulin, and IGF-1. Cytokines may be expressed by cells genetically modified, transfected or transformed, to modulate local inflammatory processes, cartilage regeneration vascularisation, etc.

The collagen can be extracted from various collagen-containing animal tissues. Examples of possible collagen-containing tissue are tendon, skin, cornea, bone, cartilage, in vertebral disc, cardiovascular system and placenta. The collagen used herein is type I collagen. Other types of collagen (e.g., type II, III and others) may also be employed.

In accordance with the most preferred embodiment of the present invention, the matrix layer 3 of the implant is composed of Type I collagen, but can be formed, and is not limited to recombinant collagen proteins as chitosan, chitin, ubiquitin, elastin, polyethylene oxide vimentin, fibronectin, and combinations thereof.

According to another aspect of the invention, there is provide an implant having a pair of generally cylindrical bone plug portions joined at their proximal ends by a core filament, the bone plug preferably including both bone regions.

In another embodiment of the present invention there is provided such an implant in which one of bone anchors 1 is adapted to be pulled through a tunnel in, for example, the femur to allow fusion thereto and the other bone anchor 1 portion is adapted to be pulled through a tunnel in the tibia to allow fusion thereto to provide a substitute for the natural cruciate ligament, the segment being adapted to be placed under tension between the tunnels to provide a ligament function. Similar procedures may be employed to provide connective tissue function to other bone joints.

One other embodiment of this invention is to provide a implant for promoting the healing and/or regrowth of diseased or damaged tissue structures by surgically repairing such structures with the implant of the invention. The implanted graft is trophic toward vascularization and tissue and may be essentially remodeled to assume the structural and functional characteristics of the repaired structure.

In accordance to another preferred embodiment of the invention, the implant may be lyophilized after its preparation. This process avoids the use of chemicals to strengthen the matrix layer 3 of the implant, to allow the reinforcement of the links between the bone plugs and the collagen layer polymerized into their trabecular structure. Also, lyophylization permits the preparation of implants adding superposed matrix layers 3 to reinforce the structure of a bioengineered connective tissue, or conferring a higher resistance to rupture before and during surgical implantation procedures.

Another important embodiment of the invention is that lyophylization may allow to form matrix layers 3 onto the implant with other biomaterials, as for example, but not limited to elastin, in combination or not with collagen, and replacing the bone anchors 1 of the implant by other porous anchors 1, as for example, but not limited to cement, or ceramic.

It is another object of the present invention to provide a graft implant which has improved graft fixation capabilities and promotes connective tissue and bone ingrowth between the graft and the bony tunnel.

In accordance with the present invention, there is provided a device and method for cyclic matrix stretching and mechanical testing. A cyclic traction machine is disclosed. In a preferred embodiment, the matrix is maintained in place in the cycling chamber by inserting the two bone anchors 1 in metal pins, one fixed to a load cell and the other, attached to a motion controlled cursor. By controlling the position of the cursor, the matrix is subjected to cyclic traction with stretching amplitudes from 0 to 30 mm at a frequency of up to 1 Hz for lower amplitudes, for any extended period of time. The whole system is controlled via a LABview VI software. The operator may change easily the traction conditions and supervise the ongoing tests to make sure that everything is running smoothly. A set of matrix may be maintained under static tension, or subjected to a cyclic tension. The cells in a matrix as described in the present invention, may be induced to take a structural organization when submitted to tension stimulus. The stimulus may be also simply waves in a culture medium by agitation of the petri dishes in which is kept a matrix, or an electric stimulus The present invention will be more readily understood by referring to the following examples which are given to illustrate the invention rather than to limit its scope.

EXAMPLE I

Preparation of Anterior Crutiate Ligament

Material and Methods

LF Isolation and Culture

Torn ACL biopsies are collected from the host. The biopsies are kept at 4° C. for no longer than 24-48 hrs before cell isolation. The ACL biopsy is weighted and cut into small pieces after removal of the periligamentous tissues. The fragments are digested with 0.125% collagenase containing 2 mM $CaCl_2$ (1 ml of enzymatic solution/mg of tissue) for 20 hrs, under gentle agitation, at 37° C. A 0.1% trypsin solution (1 ml/mg of hydrated tissue) is then added to the cellular suspension for 1 hr. The enzymes are dissolved in Dulbecco's Modification of Eagle's™ medium (Gibco), pH 7.4, containing antibiotics.

The ligament fibroblasts (LF) isolated from ACL biopsies are cultured in DME supplemented with 10% fetal calf serum (FCS), 100 IU/ml penicillin G and 25 µg/ml gentamicin (FIG. 1).

When LF primary cultures reach about 85% confluence, the cells are detached from their culture flasks using 0.05% trypsin-0.01% EDTA solution (pH 7.8), for about 10 min at 37° C. The LF suspensions are centrifuged twice at 200×g for 10 min. The cell pellets are resuspended in complete culture medium and the cells are counted. The cellular viability is determined using the trypan blue exclusion method Up until now, LF were isolated and cultured from ACL biopsies of more than 20 patents and 10 animals (goats, dogs, and rabbits) with 100% success. The cells maintained their morphology for more than 7 passages in culture. For ACL substitutes production, LF cultures from passages 2 to 5 are used. Immunofluorescent labeling analysis revealed that different populations of human LF extracted from ACL biopsies express vimentin, fibronectin, Types I and III collagens and elastin.

Preparation of the ACL Substitutes' Bone Anchors

Bone pieces are washed with ethanol 100% and cut in a cylindrical shape according to dimensions adapted to the needs of the host (average size of 1 cm-diam. and 2 cm-long).

Figure 2:
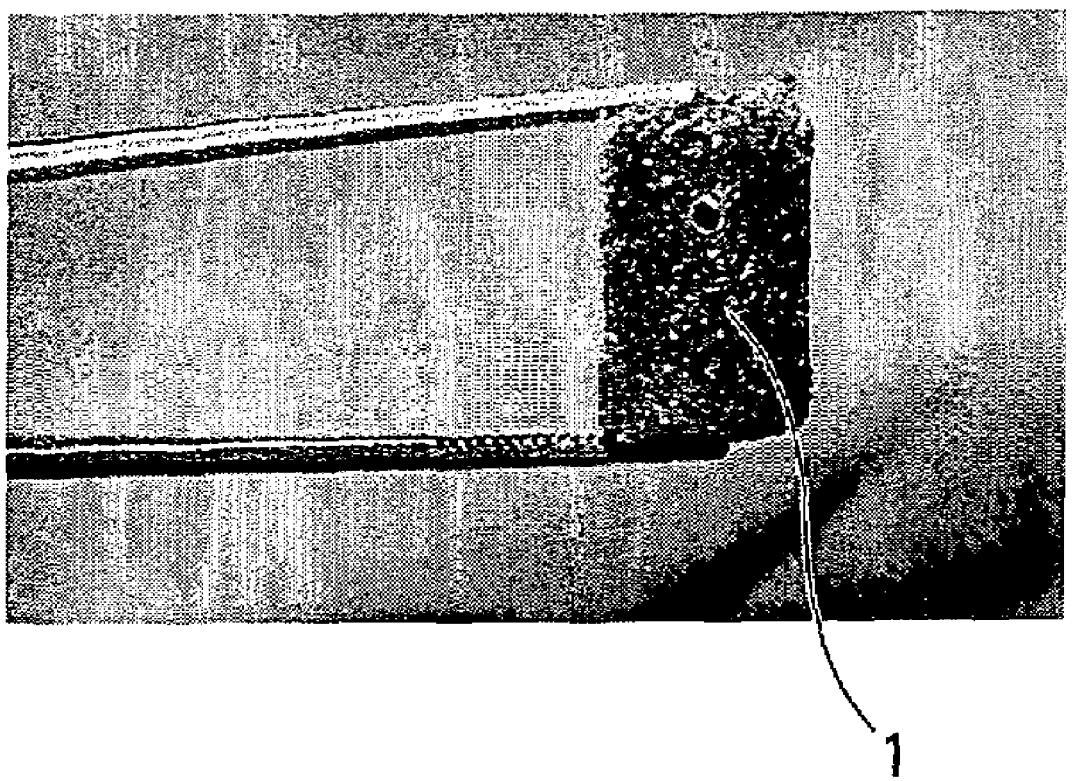
FIG. 2 illustrates a transverse hole made in a human bone anchor.
Figure 3:
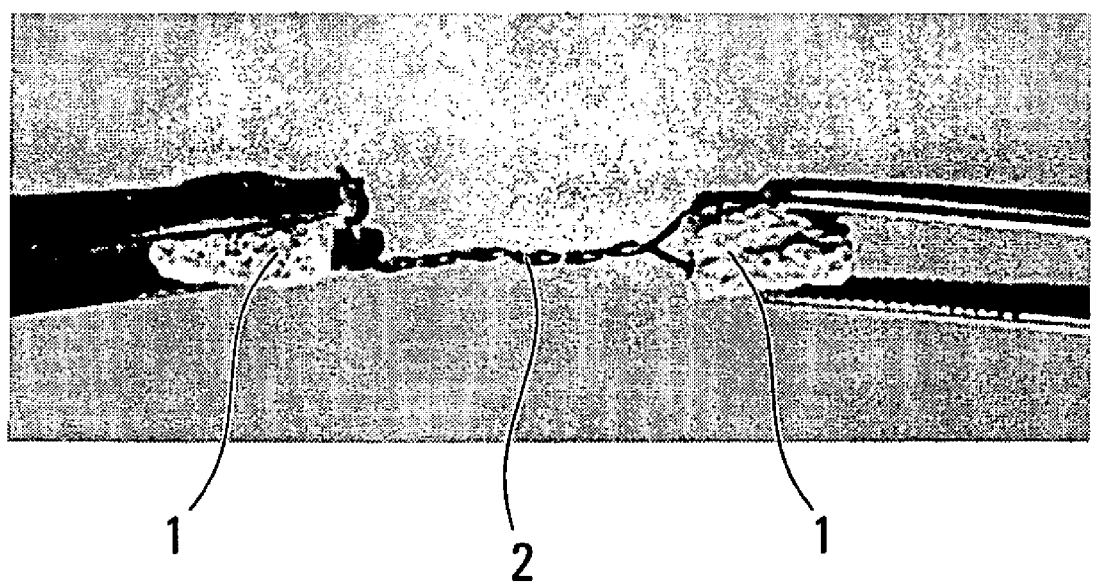
FIG. 3 illustrates two bone anchors liked with a surgical thread passed through their transverse holes and twisted.

A transverse hole (⅛-in. diam.) is made in each bone anchor 1 (FIG. 2). The bone plugs are kept in 100% ethanol overnight to be sterilized. A surgical thread resorbable within 1 month post-surgery, is passed through the transverse holes of 2 bone anchors 1 and fixed between the bones by simple stitching. Then the thread is twisted between the bones to thicken the link (FIG. 3).

Figure 4:
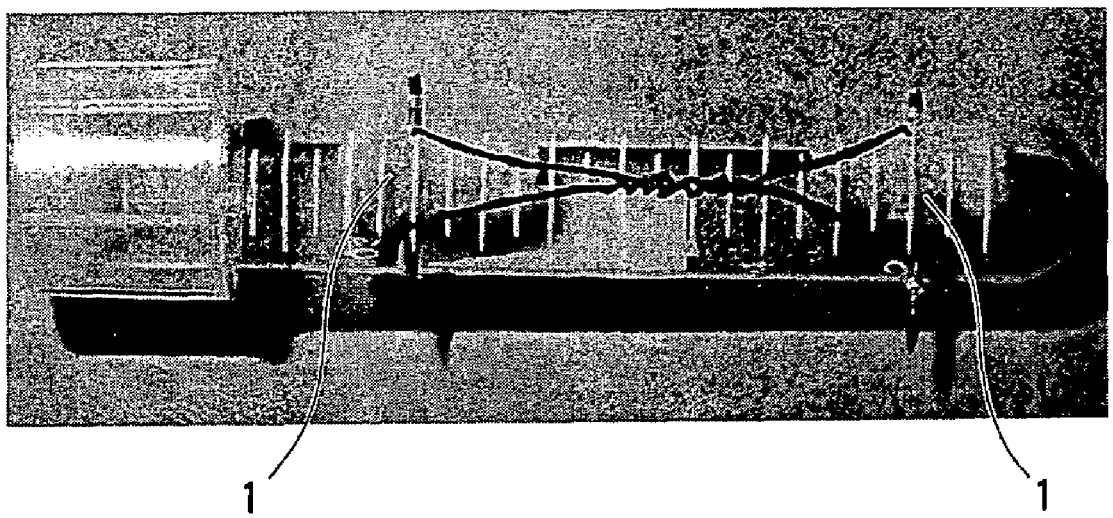
FIG. 4 illustrates two sterile bone anchors readily linked by surgical thread, transferred in a sterile plastic tube and kept in position by passing a hot metal pin through their transverses holes and across tube.

A longitudinal hole or more (1 mm diam. or wider) is made in each bone anchor 1. Such holes are drilled in order to increase hydrated collagen adhesion with the bones. This step is optional. The 2 sterile bone plugs readily linked by the twisted surgical thread are transferred in a sterile plastic tube and kept in position by passing a hot metal pin through their transverse holes and across the tube (FIG. 4).

One of the 2 bones is fixed at the bottom and the other at the top of the tube. Then, the tube containing the bone plugs are filled with sterile culture medium containing 10% FCS and put at 37° C. overnight in order to verify that no bacterial contamination comes out. Up to now, we never had any contamination following this method. Another alternative could be that the bones and thread would be rinsed with 100% ethanol, dried under sterile conditions and sterilized a second time with ethylene oxide. They could be kept in sterile culture medium containing 5-10% FCS at 4° C. until use.

Production of the Bioengineered ACL Substitutes in vitro

Two protocols have been developed to obtain similar products; graftable bioengineered ACL substitutes. The protocol involves the addition of the living LF only at the end of the production steps, avoiding the use of cell-populated collagen gels during the.

Figure 10:
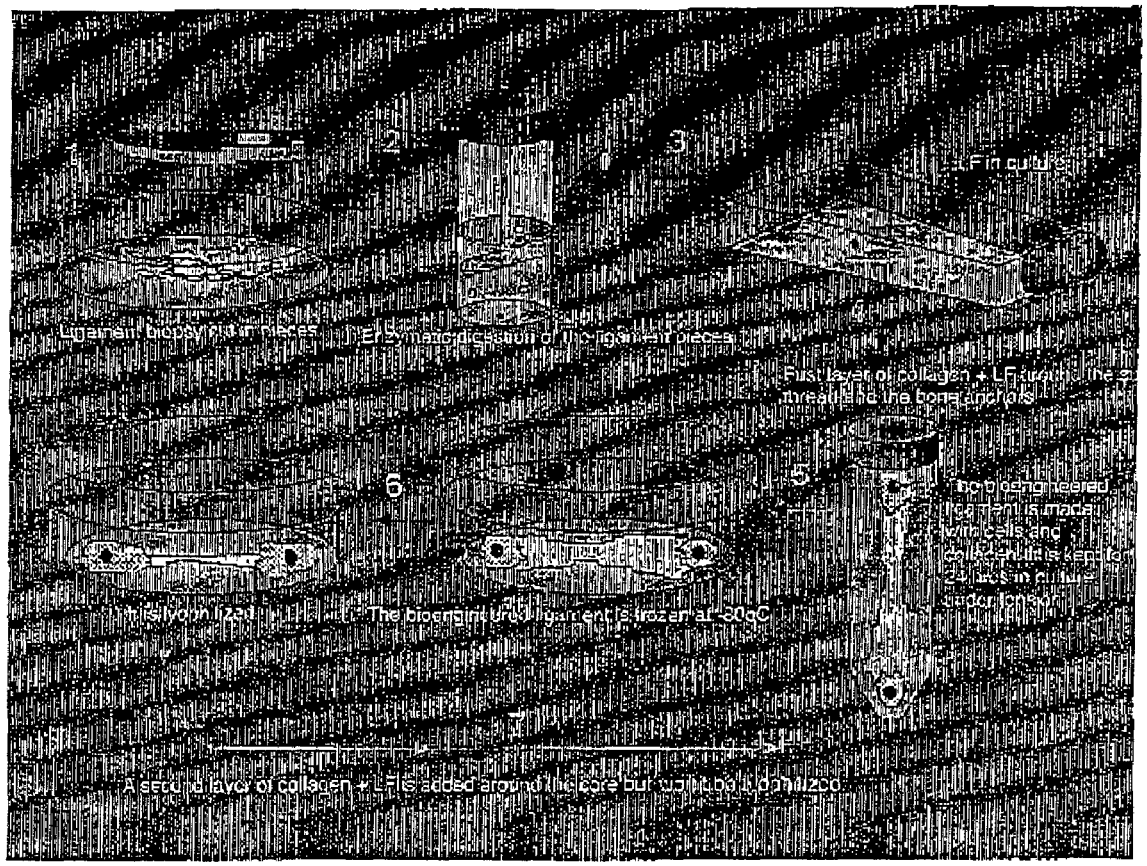
FIG. 10 illustrates the multistep procedure to prepare a substitute ligament.

A solution of DME 2.7X containing antibiotics is mixed with a second solution containing heat inactivated (30 min at 56° C.) FCS, solubilized bovine Type I collagen and living LF (preferably from passages 2 to 5; FIG. 10, step 3). The cells are added at a final concentration of $2.5 \times 10^5$ cells per ml but lower or higher cell concentrations could be used. The final concentration of bovine Type I collagen varies between 1.0-2.0 mg/ml in the ACL substitutes but other concentrations could be used (e.g. preferably ranging from 0.5 to 5 mg/ml). The next step is described on FIG. 10, step 5.

B) A solution of DME 2.7X containing antibiotics is mixed with a second solution containing heat inactivated (30 min at 56° C.) FCS, solubilized bovine Type I collagen. The final concentration of bovine Type I collagen varies between 1.0-2.0 mg/ml in the ACL substitutes but other concentrations could be used (e.g. preferably ranging from 0.5 to 5 mg/ml). There is yet no cell added in the mixture at this stage.

The mixture is quickly poured in the sterile plastic tube containing the 2 bone anchors linked by the twisted surgical thread.

Figure 5:
FIG. 5 illustrates an ACL substitute after 24 hours in culture.
Figure 6:
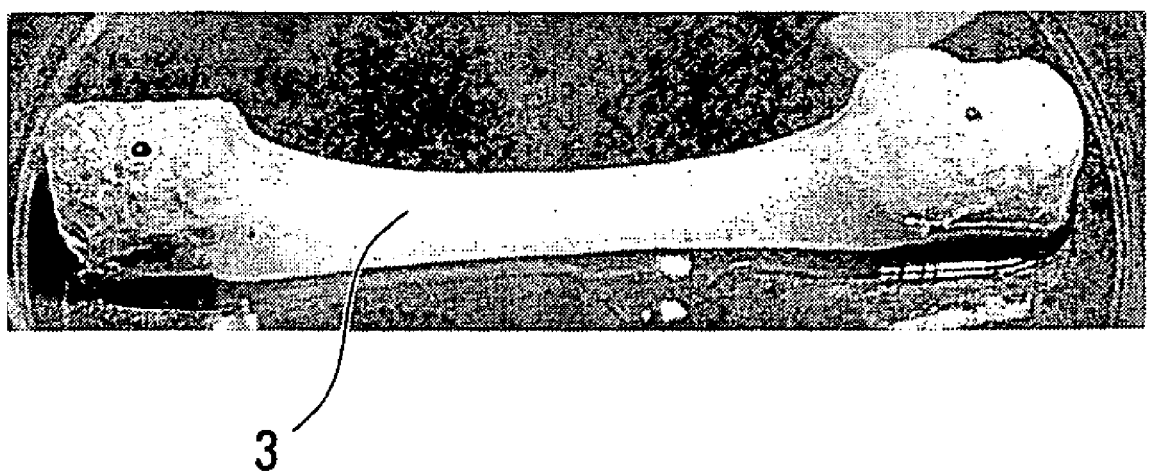
FIG. 6 illustrates an acellular ACL substitute after 24 hours in culture.

The ACL substitute is cultured in DME supplemented with 10% FCS, 50 µg/ml ascorbic acid, 100 IU/ml penicillin G and 25 µg/ml gentamicin. It is maintained in a static vertical position during the first 24 hrs of culture mainly to allow proper collagen polymerization. The ACL substitute is then taken out of the tube after collagen polymerization (at pH 7.4). The collagen matrix is also contracted when the ACL substitute contained living LF according to procedure A (FIG. 5) but it is not contracted in the case of acellular substitutes prepared as described in procedure B (FIG. 6).

Figure 11:
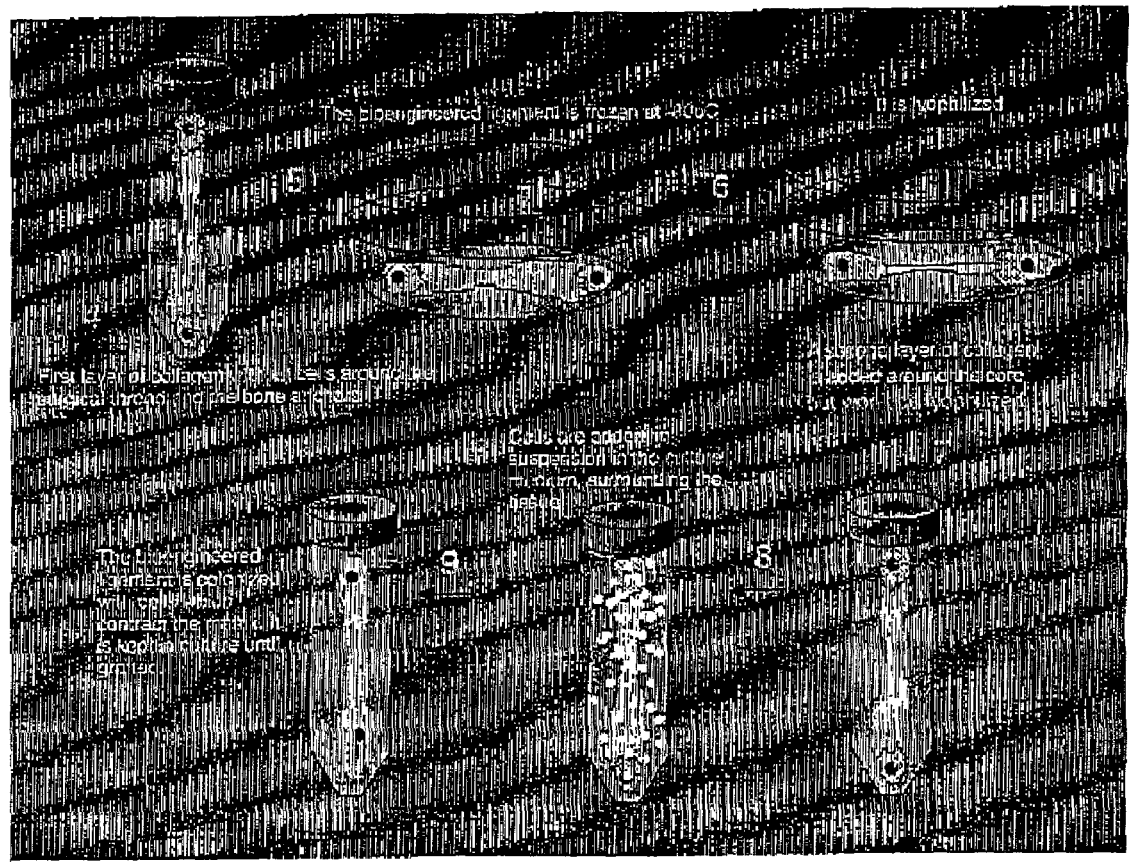
FIG. 11 illustrates an alternative multistep procedure to prepare a substitute ligament.

Then, the ACL substitute is taken out of the tube and frozen at −80° C. in a sterile dish (FIGS. 10 and 11, step 5).

Figure 7:
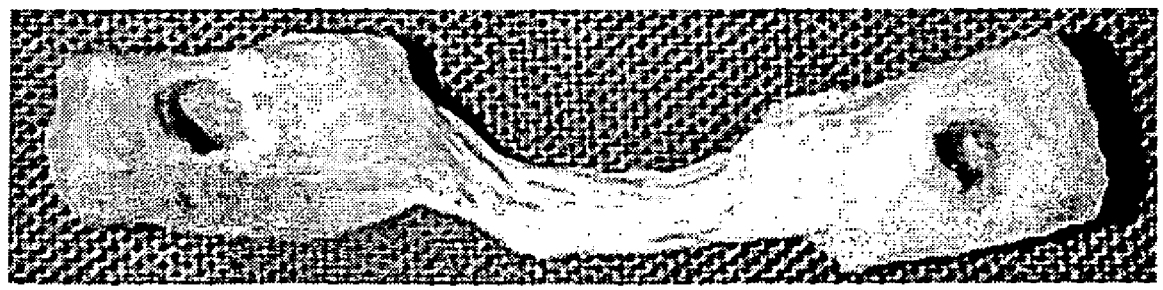
FIG. 7 illustrates an ACL substitute lyophilized.

When frozen, the ACL substitute is lyophilized (FIG. 7 and FIGS. 10 and 11, step 6).

The lyophilized ACL substitute is then transferred into a new sterile plastic tube and fixed as previously described to be used as a solid central core (FIGS. 10 and 11, step 7). Additional lyophilized layers can be added to produce larger and stronger ACL substitutes.

Figure 8:
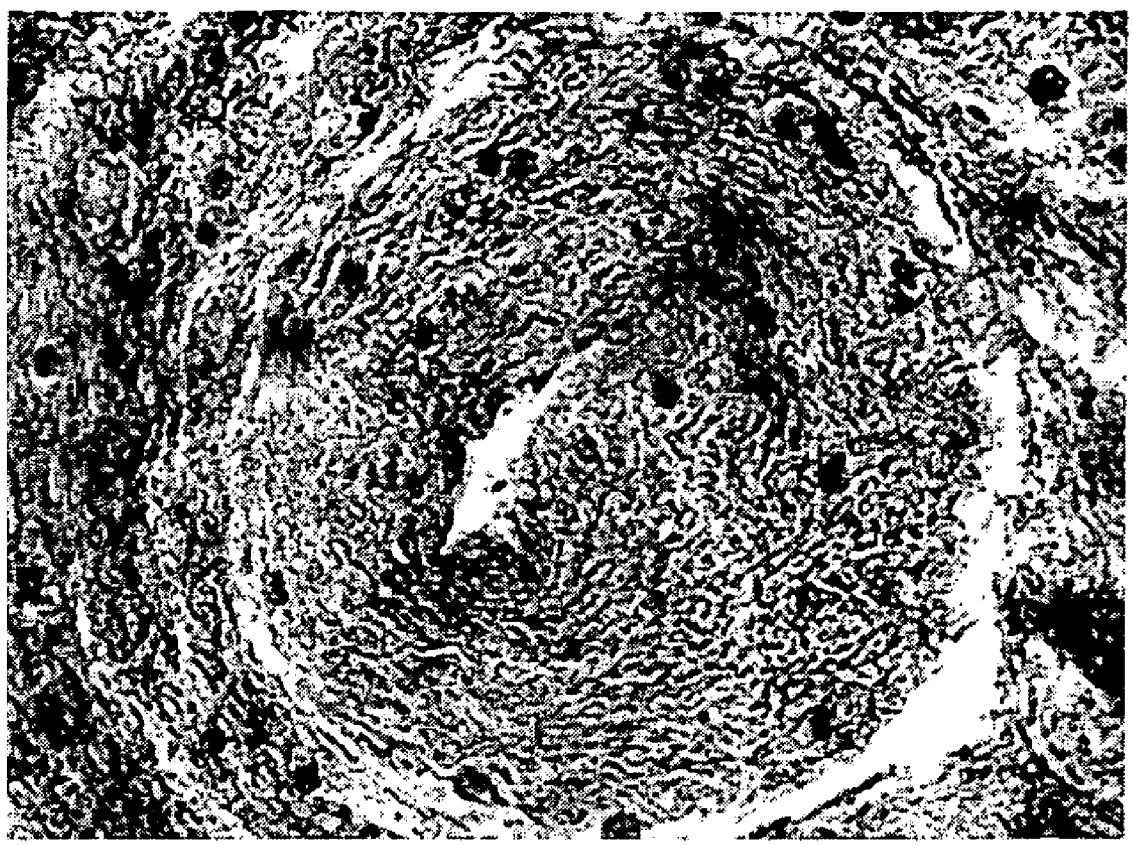
FIG. 8 illustrates a histological section of a goat's ACL substitute before implantation. The hydrated collagen layer seeded with living LF surrounds the central circular lyophilized core.

Another layer of hydrated collagen mixed with living LF is made and added around the lyophilized collagen core, according to the procedures described in section A. The bilayered ACL substitute can be kept in culture until grafted into the host. FIG. 8 shows a histological section of the ACL substitute before implantation (transversal plan). The central lyophilized core is surrounded by a hydrated collagen layer seeded with LF of the eventual host, in that case, a goat.

Figure 9:
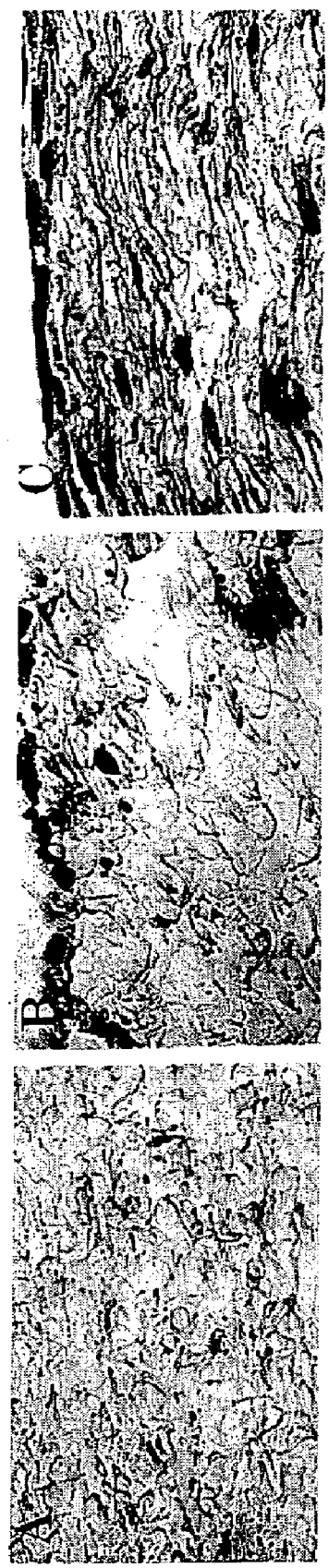
FIGS. 9A to 9C illustrate the collagen layer of an acellular ACL substitute consisting in a network of collagen fibers (A); the adhesion and migration of containing LF into the outer acellular hydrated collagen layer after 24 hours in culture (B); and same as in b) but after 48 hours of culture (C)

A second layer of hydrated collagen is made as described in section B (no cell is included within the matrix). The acellular ACL substitute is a network of collagen fibers (FIG. 9A). After its polymerization overnight, the acellular ACL substitute is put in culture medium containing LF suspended in the medium (DME supplemented with 10% FCS, 50 $\mu$g/ml ascorbic acid, 100 IU/ml penicillin G and 25 $\mu$g/ml gentamicin; FIG. 11, step 8). Within 24 hrs, the cells attach and migrate into the outer hydrated collagen layer (not lyophilized; FIG. 9B). The cells contract the collagen matrix while colonizing it within 48 hrs (FIG. 9C) The bilayered cell-populated ACL substitute can be kept in culture until grafted (FIG. 11, step 9). More hydrated matrix layers 3 can be added around the bACL.

Organization of Matricial Structure Induced in the ACL Substitute by Cyclic Traction At least 10 replicates were conducted under similar conditions to evaluate the effects of cyclic traction on the evolution of our ACL. The cycles were fixed at a frequency of 1 cycle/min. During the first 5 days, the ACL were stretched to 1-mm stretch per cycle, always returning to their initial length (about 4 cm) to complete each cycle. The amplitude was increased to 2 mm from days 5 to 10. Histologic studies were performed after 10 days on ACL cultured under static horizontal conditions compared to ACL subjected to cyclic traction. For the first time, dense network of collagen fibers organized in wavy bundles is observed in in a human bioengineered living tissue. Our data strongly show that living ACL cells seeded in ACL can respond to mechanical stimuli in vitro. The crimps followed a wavy pattern, as it is seen in native ACL. Results were repeatedly similar from one experiment to another.

Surgical Procedure for Implantation of the Bioengineered ACL Substitutes in Human and Animals Surgical procedures are performed by arthroscopy in human and under general anesthesia in animals (intramuscular injection of ketamine and xylasine; 0.6 ml/kg body weight), maintained by inhalation of a 2:1 mixture of oxygen and nitrous oxide with 0.1% halothane.

With use of Kirschner wires and a mini-driver, a tunnel (about 1 cm diam., adapted to the knee of the host) will be created through the metaphyseal bone of the femur, distal to the epiphyseal scar and perpendicular to the long axis of the femur.

The bACL (about 1 cm length, adapted to the knee of the host) is placed within the bone tunnel, with great care to ensure that the bACL fills the entire length of the hole.

The end of the prosthesis exiting the lateral end of the tunnel is inserted in a second tunnel performed in the lateral femoral periosteum. A minimal static tension is applied on the bACL.

The bone anchors 1 of the graft may be fixed with screws and/or cement (including biomedical epoxy).

The incision site is sprayed with a topical antibacterial agent. In the case of human, they receive a normal diet and movement restrictions during the first month post-surgery. They start to put weight on the operated leg according to tolerance and receive an exercise program to maintain or increase muscular strength. Their knees are monitored daily for a week to notice any abnormal inflammatory signs. In the case of animals, they receive a diet of water and food ad libitum. Prophylactic tetracycline is added in water for 10 days. A cast or a light orthosis presently used to limit human joint motions postsurgery is used to prevent animal knee motion over 4-7 days after bACL implantation. The animal's physical evaluation is done daily by veterinarians and their staff.

Such ligament substitute may be modified further or adapted for gene therapy by introducing genes into the cells. Also, the procedure may be easily adapted to other applications, for example, to replace a ligament at another anatomic site of the body (vertebral column, neck, etc).

EXAMPLE II

Preparation of Connective Tissues

Material and Methods

Dermal Fibroblasts Isolation and Culture

The dermal fibroblasts (DF) isolated from the dermis of skin biopsies, enzymatically (same procedure described in Example I) or by explants, are cultured in DME supplemented with 10% fetal calf serum (FCS), 100 IU/ml penicillin G and 25 μg/ml gentamicin.

When DF primary cultures reach about 85% confluence, the cells are detached from their culture flasks using 0.05% trypsin-0.01% EDTA solution (pH 7.8), for about 10 min at 37° C. The DF suspensions are centrifuged twice at 200×g for 10 min. The cell pellets are resuspended in complete culture medium and the cells are counted. The cellular viability is determined using the trypan blue exclusion method.

Up until now, the DF were isolated and cultured from skin biopsies of more than hundred patients and 10 animals (goats, dogs, and rabbits) with 100% success. The cells maintained their morphology for more than 7 passages in culture. For connective tissue substitutes production (e.g. ligaments), DF cultures from passages 2 to 5 are used.

Preparation of the Ligament Substitutes' Bone Anchors

Bone pieces are washed, cut and sterilized according to the procedure described in Example I.

Holes are made in each bone anchor 1 as previously described. The 2 sterile bone plugs readily linked by the twisted surgical thread are transferred in a sterile plastic tube and kept in position by passing a hot metal pin through their transverse holes and across the tube (FIG. 4).

Production of Bioengineered Ligament Substitutes in vitro

A first alternative: A solution of DME 2.7X containing antibiotics is mixed with a second solution containing heat inactivated (30 min at 56° C.) FCS, solubilized bovine Type I collagen and living DF (preferably from passages 2 to 5). The DF are added at a final concentration of $2.5 \times 10^5$ cells per ml but lower or higher cell concentrations could be used. The final concentration of bovine Type I collagen varies between 1.0-2.0 mg/ml in the ligament substitutes but other concentrations could be used (e.g. preferably ranging from 0.5 to 5 mg/ml). The next step is described in FIG. 11 step 5).

A second alternative: A solution of DME 2.7X containing antibiotics is mixed with a second solution containing heat inactivated (30 min at 56° C.) FCS, solubilized bovine Type I collagen. The final concentration of bovine Type I collagen varies between 1.0-2.0 mg/ml in the ACL substitutes but other concentrations could be used (e.g. preferably ranging from 0.5 to 5 mg/ml). There is yet no cell added in the mixture at this stage.

Figure 12:
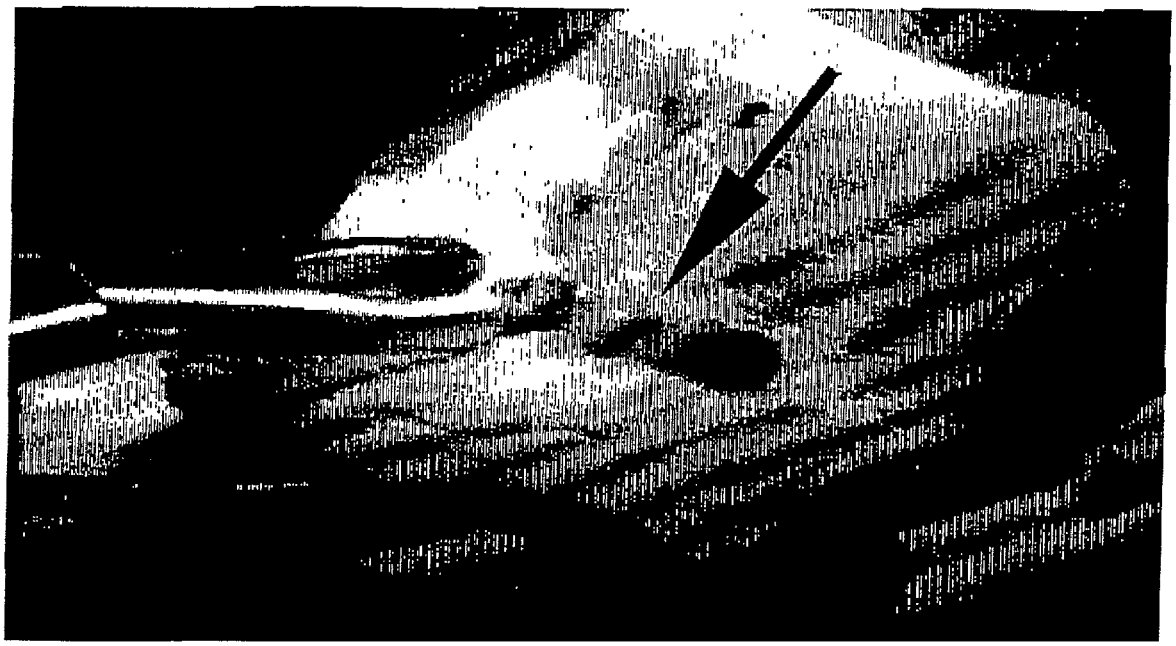
FIG. 12 and illustrates a macroscopic aspect of a bioengineered ACL ready for implantation (opened goat's knee joint)
Figure 13:
FIG. 13 illustrates a macroscopic aspect of a bioengineered ACL immediately after implantation in situ (opened goat's knee joint)
Figure 14:
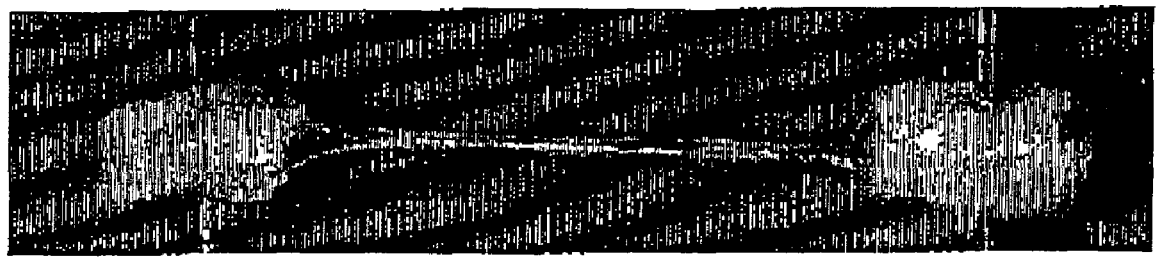
FIG. 14 illustrates the macroscopic aspect of a dehydrated ligament substitute.
Figure 15:
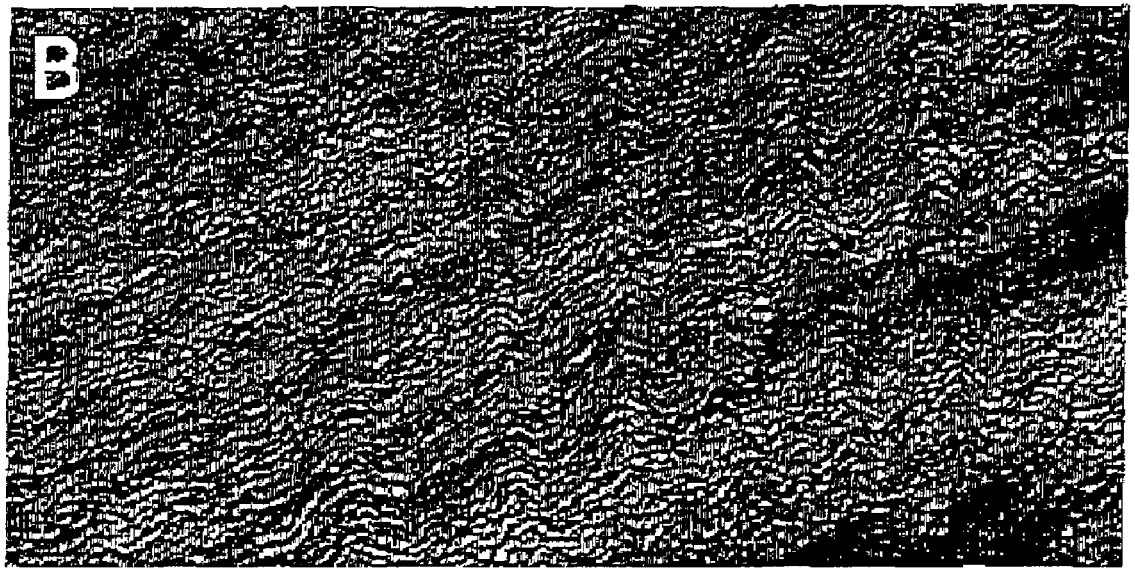
FIG. 15 illustrates an histological section of a dehydrated ligament substitute showing an alignment of the collagen fibers in its scaffold (longitudinal plan)

The mixture is quickly poured in the sterile plastic tube containing the 2 bone anchors 1 linked by the twisted surgical thread. Collagen scaffolds are casted between two bone anchors 1 described in example I. The tissue constructs are put into a dessicator under minimal horizontal tension, under normal atmospheric pressure or less (ranging from about 25 to 0 mm Hg). The appearance of the macroscopic aspect of a bioengineered ACL ready for implantation can be seen in FIG. 12, as well as immediately after implantation in situ (opened goat's knee joint) (FIG. 13). The scaffolds were completely dehydrated within about 2-3 hrs (FIG. 14). FIG. 15 shows a histological section of a collagen matrix dehydrated under these conditions.

The bioengineered scaffolds were rehydrated in fresh DMEM, taken out of the tube and then transferred into a new sterile plastic tube. Additional dehydrated layers can be added or another layer of hydrated collagen can be added containing living DF or LF, to produce larger and stronger ligament substitutes.

Figure 16:
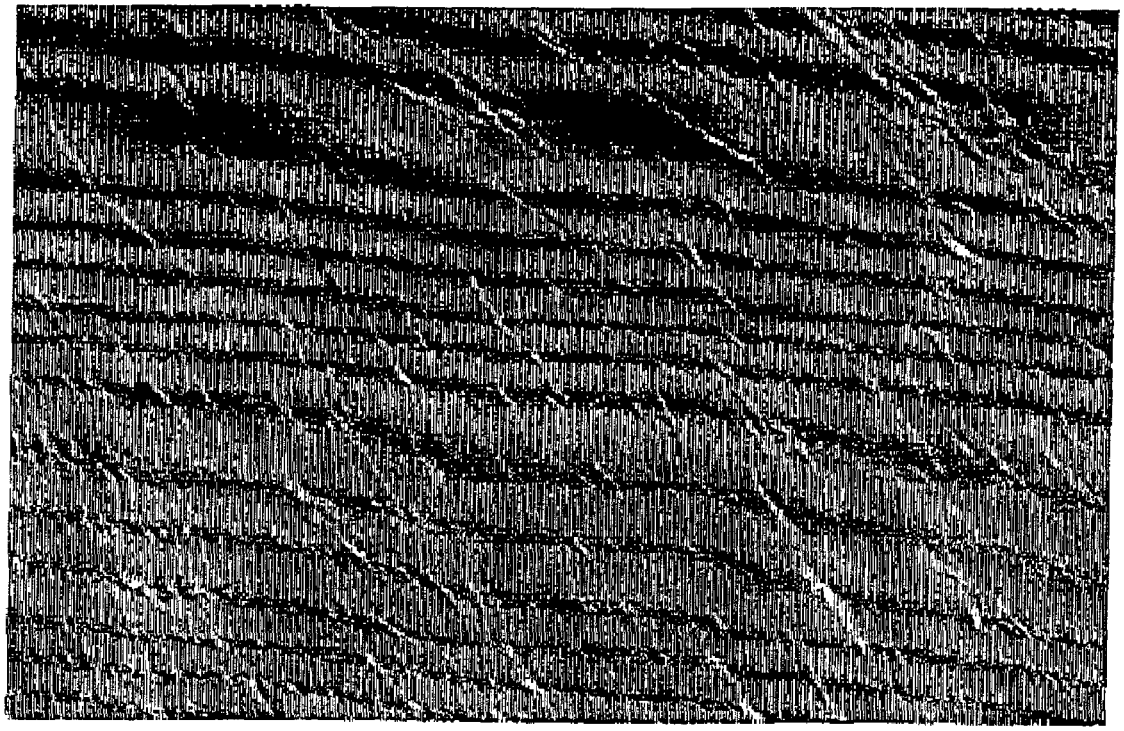
FIG. 16 illustrates an histological section of an acellular ligament substitute grafted in a goat's knee joint for 5 months.

An acellular bioengineered ligament has been grafted into a goat's knee joint. After five months, as shown in FIG. 16, the grafted ligament is clearly colonized and innervated by the hosts' cells. Note the presence of the host's cells which colonized the graft post-implantation and the high density of collagen fibers, aligned in the long axis of the regenerating anterior cruciate ligament in situ (longitudinal plan).

EXAMPLE III

Preparation of Periodontal Ligament Substitute

Material and Methods

Fibroblasts Isolation and Culture

Dermal fibroblasts (DF), ligament fibroblasts (LF), or fibroblasts from other sources (e.g. mucosa of the mouth) can be isolated and cultured in DME supplemented with 10% fetal calf serum (FCS), 100 IU/ml penicillin G and 25 µg/ml gentamicin.

When the cells primary cultures reach about 85% confluence, they are detached from their culture flasks using 0.05% trypsin-0.01% EDTA solution (pH 7.8), for about 10 min at 37° C. The cell suspensions are centrifuged twice at 200×g for 10 min. The cell pellets are resuspended in complete culture medium and the cells are counted. The cellular viability is determined using the trypan blue exclusion method.

Preparation of the Peridontal Ligament Substitutes' Tooth Anchors

Teeth pieces are washed and sterilized according to the procedure described in Example I.

Holes are made in each tooth, as previously described. A sterile tooth is linked to a bone anchor 1 by a twisted surgical thread and both are transferred in a sterile plastic tube and kept in position by passing a hot metal pin through their transverse holes and across the tube.

Production of Bioengineered Peridontal Ligament Substitutes in vitro

A solution of DME 2.7X containing antibiotics is mixed with a second solution containing heat inactivated (30 min at 56° C.) FCS, solubilized bovine Type I collagen and living fibroblasts (preferably from passages 2 to 5). The fibroblasts are added at a final concentration of $2.5 \times 10^5$ cells per ml but lower or higher cell concentrations could be used. The final concentration of bovine Type I collagen varies between 1.0-2.0 mg/ml in the ligament substitutes but other concentrations could be used (e.g. preferably ranging from 0.5 to 5 mg/ml).

According to a second possibility, a solution of DME 2.7X containing antibiotics is mixed with a second solution containing heat inactivated (30 min at 56° C.) FCS, solubilized bovine Type I collagen. The final concentration of bovine Type I collagen varies between 1.0-2.0 mg/ml in the ACL substitutes but other concentrations could be used (e.g. preferably ranging from 0.5 to 5 mg/ml). There is yet no cell added in the mixture at this stage.

Figure 17:
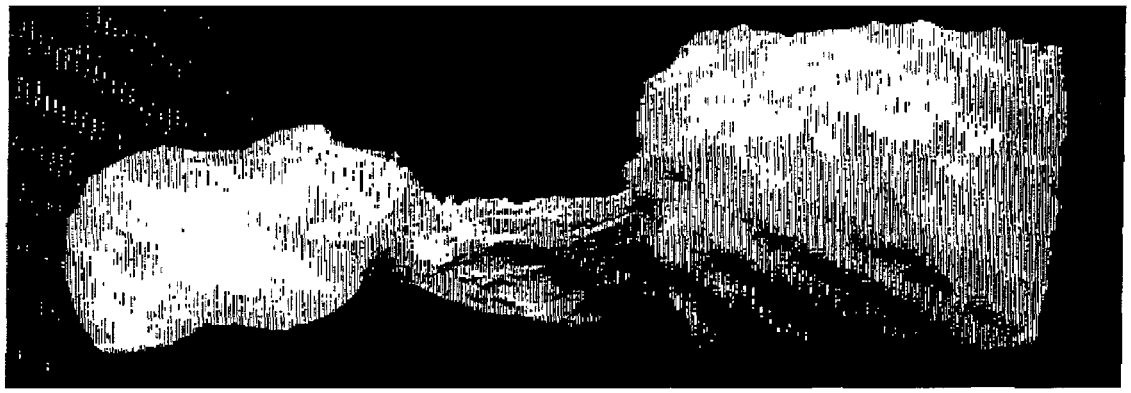
FIG. 17 illustrates the macroscopic aspect of a bioengineered periodontal ligament ready for implantation.

The mixture is quickly poured in the sterile plastic tube containing the bone and the tooth anchors 1 linked by the twisted surgical thread. Collagen scaffolds are casted between two anchors 1. The tissue constructs are lyophilized or put into a dessicator under minimal horizontal tension, under normal atmospheric pressure or less (ranging from about 25 to 0 mm Hg). When totally dehydrated, the scaffolds are rehydrated in fresh DMEM, taken out of the tube and then transferred into a new sterile plastic tube. Another layer of hydrated collagen can be added containing living fibroblasts, to produce larger and stronger ligament substitutes. The periodontal ligament substitute can be implanted in the gum (FIG. 17).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An implant for connective tissue substitution in an animal, said implant comprising:
   (a) a pair of bone anchors;
   (b) at least one support filament joining said bone anchors at their proximal ends, said bone anchors having been joined with said support filament ex vivo; and
   (c) at least one matrix layer coating said support filament, wherein said matrix layer is in contact with said bone anchors;
   wherein said matrix layer is of sufficient thickness to allow for colonization by a cell and wherein said implant in its entirety is dehydrated or lyophilized prior to implantation.

2. The implant according to claim 1, wherein said matrix layer is colonized by a cell.

3. The implant according to claim 1, wherein said connective tissue substitution is partial or complete substitution of a connective tissue.

4. The implant according to claim 1, wherein said connective tissue is selected from the group consisting of a tendon, a cartilage, a disk, a meniscus, a muscle, a tooth, a hair, a joint, and a ligament, or a combination thereof.

5. The implant according to claim 1, wherein said animal is a human.

6. The implant according to claim 1, wherein said animal is a non-human mammal.

7. The implant according to claim 1, wherein said bone anchor is selected from the group consisting of a bone portion and a piece composed of (a) a natural biocompatible porous material; (b) a synthetic biocompatible porous material; or (c) both (a) and (b).

8. The implant according to claim 1, wherein said matrix layer is a collagen gel layer.

9. The implant according to claim 8, wherein said collagen is a recombinant collagen.

10. The implant of claim 8, wherein said collagen is selected from the group consisting of types I, II and III collagen.

11. The implant of claim 8, wherein the collagen is from an animal tissue source.

12. The implant of claim 11, wherein said animal tissue is selected from the group consisting of tendon, skin, cornea, bone, cartilage, vertebral disc, cardiovascular tissue and placenta.

13. The implant according to claim 1, wherein said matrix layer is selected from the group consisting of chitosan, glycosaminoglycan, chitin, ubiquitin, elastin, polyethylene glycol, polyethylene oxide, vimentin, fibronectin, and a protein promoting collagen alignment or assembly, or derivatives or a combination thereof.

14. The implant according to claim 1, wherein said support filament is selected from the group consisting of at least one of a resorbable thread, a natural fiber, and a filament composed of a protein, a lipid, a biocompatible molecule, or a synthetic component.

15. The implant according to claim 1, wherein said matrix layer further comprises a cell.

16. The implant according to claim 15, wherein said cell is an autologous cell.

17. The implant according to claim 15, wherein said cell is a heterologous cell.

18. The implant according to claim 1, wherein said cell is selected from the group consisting of a fibroblast, a myoblast, an osteoblast, a mesenchymal cell, an endothelial cell, an immune cell, and a chondrocyte cell, or a combination thereof.

19. The implant according to claim 1, wherein said matrix layer further comprises a phannaceutically effective amount of a biologically active molecule selected from the group consisting of a drug, a growth factor, a cytokine, an antibiotic, and a hormone, or a combination thereof.

20. The implant according to claim 1, wherein said matrix layer further comprises at least one inner layer of gel and/or filament coated by at least one supplementary matrix coating layer.

21. The implant according to claim 20, wherein said inner layer is dehydrated and said filament is dehydrated or lyophilized prior to being incorporated to said matrix layer.

22. The implant according to claim 20, wherein said implant is dehydrated or lyophilized prior to coating with said supplementary matrix coating layer.

23. The implant according to claim 22, wherein said supplementary matrix coating layer is further dehydrated or lyophilized before being coated by another supplementary matrix coating layer.

24. The implant according to claim 20, wherein said matrix coating layer further comprises a cell.

25. The implant according to claim 24, wherein said cell is an autologous cell.

26. The implant according to claim 24, wherein said cell is a heterologous cell.

27. The implant according to claim 24, wherein said cell is selected from the group consisting of a fibroblast, a myoblast, an osteoblast, a mesenchymal cell, an endothelial cell, an immune cell, and a chondrocyte, or a combination thereof.

28. The implant of claim 1, wherein said implant is a ligament substitute.

29. The implant of claim 13, wherein said ligament substitute is selected from the group consisting of an anterior cruciate ligament substitute and a periodontal ligament substitute.

* * * * *

UNITED STATES PATENT AND TRADEMARK OFFICE
CERTIFICATE OF CORRECTION

PATENT NO. : 7,335,230 B2 Page 1 of 1
APPLICATION NO. : 09/990320
DATED : February 26, 2008
INVENTOR(S) : Lucie Germain et al.

It is certified that error appears in the above-identified patent and that said Letters Patent is hereby corrected as shown below:

Title Page:

Item (75), Inventors: "St-Etinne-de-Lauzon" should be -- St-Etienne-de-Lauzon --.

Assignee (73), please add -- Université Laval, Québec (CA) --.

Assignee (73), "Universite de Montreal, Montreal (CA)" should be -- Université de Montréal, Montréal (CA) --.

Signed and Sealed this

First Day of December, 2009

David J. Kappos
*Director of the United States Patent and Trademark Office*